US008932570B2

(12) United States Patent
Mu et al.

(10) Patent No.: US 8,932,570 B2
(45) Date of Patent: Jan. 13, 2015

(54) LONG-WEARING GLOSSY COSMETIC COMPOSITION

(75) Inventors: Weilin Mu, Albertston, NY (US); Linda Carol McKenna, North Bablyon, NY (US); George J. Stepniewski, Melville, NY (US); Dexin Luo, Fresh Meadows, NY (US); Shanan Nazar, Garden City, NY (US); Tian Xiang Wang, Dix Hills, NY (US)

(73) Assignee: ELC Management LLC, New York, NY (US)

( * ) Notice: Subject to any disclaimer, the term of this patent is extended or adjusted under 35 U.S.C. 154(b) by 405 days.

(21) Appl. No.: 12/730,350

(22) Filed: Mar. 24, 2010

(65) Prior Publication Data

US 2011/0073126 A1 Mar. 31, 2011

Related U.S. Application Data

(63) Continuation-in-part of application No. 11/127,938, filed on May 12, 2005, now abandoned.

(51) Int. Cl.
*A61K 8/85* (2006.01)
*A61K 8/81* (2006.01)
*A61K 8/86* (2006.01)
*A61Q 1/04* (2006.01)
*A61Q 1/10* (2006.01)

(52) U.S. Cl.
CPC ............... *A61K 8/8152* (2013.01); *A61K 8/86* (2013.01); *A61Q 1/04* (2013.01); *A61Q 1/10* (2013.01)
USPC ..................................... 424/78.02

(58) Field of Classification Search
None
See application file for complete search history.

(56) References Cited

U.S. PATENT DOCUMENTS

| | | |
|---|---|---|
| 3,927,199 A | 12/1975 | Micchelli et al. |
| 4,946,932 A | 8/1990 | Jenkins |
| 4,980,155 A | 12/1990 | Shah et al. |
| 4,988,502 A | 1/1991 | Ounanian et al. |
| 5,199,980 A | 4/1993 | Lynch et al. |
| 5,266,322 A | 11/1993 | Myers et al. |
| 5,288,493 A | 2/1994 | Martino et al. |
| 5,496,543 A | 3/1996 | Lagrange et al. |
| 5,843,407 A | 12/1998 | El-Nokaly et al. |
| 5,846,551 A | 12/1998 | DaCunha et al. |
| 5,879,668 A | 3/1999 | Hanna et al. |
| 5,925,337 A | 7/1999 | Arraudeau et al. |
| 5,948,419 A | 9/1999 | Bankert et al. |
| 6,060,547 A | 5/2000 | Canter et al. |
| 6,139,827 A | 10/2000 | Cohen et al. |
| 6,296,858 B1 | 10/2001 | Agostini et al. |
| 6,303,105 B1 | 10/2001 | Shah et al. |
| 6,326,013 B1 | 12/2001 | Lemann et al. |
| 6,361,781 B2 | 3/2002 | Lorant |
| 6,399,050 B1 | 6/2002 | Pasquet et al. |
| 6,444,212 B1 | 9/2002 | Cavazzuti et al. |
| 6,458,390 B1 | 10/2002 | Manelski et al. |
| 6,500,439 B1 | 12/2002 | Morita et al. |
| 6,531,119 B1 | 3/2003 | Hall-Puzzio et al. |
| 6,558,697 B2 | 5/2003 | Cannell et al. |
| 6,726,900 B2 | 4/2004 | Scancarella et al. |
| 6,780,422 B2 | 8/2004 | Brieva et al. |
| 7,323,162 B2 | 1/2008 | Martin et al. |
| 2001/0055600 A1 | 12/2001 | Shah |
| 2004/0126346 A1* | 7/2004 | Martin et al. ............ 424/64 |
| 2004/0265258 A1 | 12/2004 | Robinson et al. |
| 2006/0182773 A1 | 8/2006 | Bruning et al. |

FOREIGN PATENT DOCUMENTS

| | | |
|---|---|---|
| CA | 2233342 | 10/1998 |
| CA | 2396621 | 8/2001 |
| CA | 2479106 | 11/2003 |
| CA | 2474708 | 7/2004 |
| FR | 2783162 | 3/2000 |
| FR | 2845278 | 4/2004 |
| WO | WO99/44576 | 9/1999 |
| WO | WO2004/030606 | 4/2004 |

OTHER PUBLICATIONS

Garruto et al., Cos. & Toilet., 2001, 116(3), pp. 73-76.*
Supplemental European Search Report; EP06759776.5: Completion Date: Dec. 20, 2011: Mailing Date: Dec. 29, 2011.
http://findarticles.comp/articles/mi_hb3042/is_1_38/ai_n28822646/; Retail Industry; Garruto, John A.; Novel Water Compatible Esters for Personal Care; Household & Personal Products Industry; vol. 38; pp. 71-74; Jan. 2001. (9 pgs. Submitted—full article).
PCT International Search Report; International Application No. PCT/US06/18604; Completion Date: Sep. 9, 2006; Date of Mailing: Oct. 12, 2006.
PCT Written Opinion of the International Searching Authority, or the Declaration; Completion Date: Sep. 12, 2006; Date of Mailing: Oct. 12, 2006.
Diamond, Kerry; Get Bigger, Sexy Lips; Harper's Bazaar Spring Fashion Issue; p. 340; Mar. 2004. (4 pgs. Submitted).
Garruto, John A.; Specialty Esters for Aqueous Systems; Cos. & Toilet Magazine; vol. 116; No. 3; pp. 73-76; Mar. 2001.

* cited by examiner

*Primary Examiner* — Brian Gulledge
(74) *Attorney, Agent, or Firm* — Cynthia R. Miller

(57) ABSTRACT

A transfer-resistant, single phase aqueous cosmetic compositions are provided. The compositions consist essentially of a water-soluble, film-forming acrylates copolymer and a water-soluble plasticizer for the copolymer. The compositions contain no oils, waxes, surfactants or emulsifiers, are water- and oil-resistant upon drying on the skin, and exhibit high gloss and long-wear and transfer-resistant properties. Compositions containing pigment also demonstrate high color intensity. The compositions are useful as eyeliner, mascara, lipgloss, lipliner, and other cosmetic products.

30 Claims, No Drawings

LONG-WEARING GLOSSY COSMETIC COMPOSITION

This application is a continuation in part and claims benefit of application Ser. No. 11/127,938, filed May 12, 2005 now abandoned, the contents of which are herein incorporated by reference.

FIELD OF THE INVENTION

The present invention relates to cosmetic compositions for application to the skin, including the lips and the eyelids, and to the eyelashes. The present invention also relates to cosmetic compositions, which, when dried, after application to the skin or eyelashes, exhibit excellent water- and oil-resistance and long-wear properties, and which do not readily transfer to clothing or to other surfaces. The invention also relates to cosmetic compositions that contain substantially no oils, and yet demonstrate high gloss and color intensity. The invention further relates to aqueous cosmetic compositions that do not require emulsifiers or surfactants which are typically needed to stabilize emulsion formulations.

BACKGROUND OF THE INVENTION

Vivid color, shine and long wear are desirable properties for makeup products, particularly for eyeliner and lipgloss.

Eyeliner is a particularly desirable beautifying product. It is preferred that eyeliner be intensely colored and shiny. To achieve an intensely colored black eyeliner, for example, many prior art compositions use carbon black. However, the use of carbon black results in a cosmetic product with a less than desirable level of gloss. The use of black iron oxide in other typical eyeliner formulations containing acrylates polymers and/or copolymers has resulted in products that lacked a desirable level of color intensity, since the polymers, in most cases, are white and opaque. When the polymers dry, the film is matte or exhibits a metallic or plastic shine, which generally is not desired by consumers.

However, by using water-soluble plasticizers in combination with water-soluble polymers, in a single phase aqueous system, a transparent matrix or base is obtained that, after drying, forms a film with an oil-like shine. The high gloss intensifies the hue of colorant-containing compositions, such as mascara and eyeliner, lipliners and lipglosses, providing a rich, deep color. The lipliners and lipglosses prepared according to the invention are particularly shiny and brilliantly colored. Moreover, the water- and oil-resistance and transfer-resistance properties of the lipliner products produced enable the user to enlarge or reduce the appearance of the size of the lips which is also highly desired by consumers.

A long-wearing product that resists smudging, running and/or or fading upon exposure to oils and perspiration or tears also would be appreciated by consumers. The present invention provides transfer-resistant and water- and oil-resistant film that is long-wearing.

Non-transfer acrylates polymer-containing cosmetic compositions typically have been provided in the form of emulsions containing oils, surfactants, and/or emulsifiers or anhydrous formulations containing volatile components such as oils or alcohols. One example of such compositions is described in U.S. Pat. No. 7,323,162. The compositions exemplified are silicone in water emulsions comprising a water phase, an oil phase, and two kinds of film formers demonstrating particular solubility and surface tension parameters, a water-soluble (oil resistant) film former, such as Covacryl A15 or E14, and an oil soluble (water resistant) film former, at least one of which is a butyl acrylate/hydroxypropyl dimethicone acrylate copolymer which is a silicone-modified acrylates copolymer (e.g., Granacrylcil BAS). The compositions further include a surfactant which is specifically adapted to stabilize silicone in water emulsions, e.g., DOW 5225C formulation aid.

Nevertheless, products that do not contain emulsifiers, surfactants, oils and alcohols which may irritate or dry the skin, including the lips, of the user have become more desirable. Surfactants and/or wetting agents typically have been used in cosmetic compositions for dispersing solid pigments. Such agents tend to absorb moisture because of their chemical natures. Thus the integrity of the film formed after the composition has been applied and has dried may be compromised. In the compositions of the subject invention, however, the pigments, particularly metallic oxides, are readily dispersible in the aqueous system without dispersing agents or surfactants due to the unique combination of water-soluble plasticizers and acrylates copolymers. The pigments interacting with the water-soluble components form ultra-fine particles which increase the smoothness of the film formed. An eyeliner with as high coverage as a composition using carbon black is provided, but with a dewy appearance which is much preferred by consumers. The water- and oil-resistance properties of the compositions enhance their transfer-resistance.

In contrast with two phase oil and water emulsion systems, the compositions of the present invention are less complex and less costly to formulate, requiring only a single aqueous phase, and no oils, surfactants, or emulsifiers. Additionally, the compositions may be formulated with a single type of water-soluble film former.

SUMMARY OF THE INVENTION

The invention relates to cosmetic compositions containing acrylates copolymers which are truly water-soluble yet surprisingly demonstrate both water-resistance and transfer-resistance upon drying on the skin, including the lips and the eyelids, and on the eyelashes.

In accordance with a first aspect of the present invention, there is provided a transfer-resistant, single phase aqueous cosmetic composition, consisting essentially of
  (a) a water-soluble film-forming acrylates copolymer consisting essentially of a monomer selected from the group consisting of acrylic acid and methacrylic acid and a comonomer selected from the group consisting of alkyl and alkoxyl acrylates and alkyl and alkoxyl methacrylates;
  (b) a water-soluble plasticizer for the copolymer; and, optionally,
  (c) pigment.

In one preferred embodiment of the invention, the compositions include one type of water-soluble film former. In another preferred embodiment of the invention, the compositions contain two types of water-soluble film formers.

In accordance with a further aspect of the present invention, there is provided a method of improving the transfer-resistance and/or the shine of a cosmetic composition, comprising combining ingredients consisting essentially of:
  (a) a water-soluble film-forming acrylates copolymer consisting essentially of a monomer selected from the group consisting of acrylic acid and methacrylic acid and a comonomer selected from the group consisting of alkyl and alkoxyl acrylates and alkyl and alkoxyl methacrylates;

(b) a water-soluble plasticizer for the copolymer;
(c) water; and, optionally,
(d) pigment.

The present invention also concerns a method of redefining the lipline, comprising:
(a) providing a transfer-resistant single phase aqueous composition consisting essentially of
   (1) a water-soluble film-forming acrylates copolymer consisting essentially of a monomer selected from the group consisting of acrylic acid and methacrylic acid and a comonomer selected from the group consisting of alkyl and alkoxyl acrylates and alkyl and alkoxyl methacrylates;
   (2) a water-soluble plasticizer for the copolymer; and
   (3) pigment having a natural lip color;
(b) providing a transfer-resistant single phase aqueous composition consisting essentially of
   (1) a water-soluble film-forming acrylates copolymer consisting essentially of a monomer selected from the group consisting of acrylic acid and methacrylic acid and a comonomer selected from the group consisting of alkyl and alkoxyl acrylates and alkyl and alkoxyl methacrylates;
   (2) a water-soluble plasticizer for the copolymer; and
   (3) pigment having a desired color;
(c) dipping a lipliner brush into the composition having the natural lip color so as to load the brush with the composition;
(d) tracing a line with the lipliner brush just inside or just outside a user's natural lipline;
(e) allowing the traced line to dry;
(f) dipping a lipliner brush into the composition having the desired lip color so as to load the brush with the composition; and
(g) applying the desired color composition within the redefined lipline.

Optionally, a lipgloss, comprising the transfer-resistant single phase aqueous composition of the invention, optionally containing pigment, may be applied over the desired shade.

By use of the term "consisting essentially of" herein, it is intended that the compositions and methods of the invention contain no further component or step which would materially affect the basic and novel characteristics of the claimed invention.

Surprisingly, the compositions of the present invention contain substantially no oils or waxes, and preferably no oils or waxes, and yet exhibit high gloss and color intensity. As the single phase aqueous compositions of the invention contain essentially no oils, they do not require the surfactants and emulsifiers which are used to maintain the stability of two-phase formulations. The compositions of the invention also are water- and oil-resistant although they contain only water-soluble (oil-resistant) film formers, and no oil soluble (water-resistant) film formers.

DETAILED DESCRIPTION OF THE INVENTION

The novel cosmetic compositions of the invention are single phase aqueous formulations consisting essentially of a water-soluble film-forming acrylates copolymer, consisting essentially of a monomer selected from the group consisting of acrylic acid and methacrylic acid and a comonomer selected from the group consisting of alkyl and alkoxyl acrylates and alkyl and alkoxyl methacrylates; a water-soluble plasticizer for the copolymer, preferably, a water-soluble ester; and optionally, pigment. By "single phase" it is intended that the composition is in a stable homogeneous form rather than in the form of a heterogeneous water-in-oil or oil-in-water emulsion. The film-forming acrylates copolymer and the plasticizer are solublized in that single phase. Pigments, if any are present, are dispersed throughout the liquid in sufficiently small particles to remain stable in the composition. The copolymer, once dried, is neither water- nor oil-soluble. The unique combination of a film-forming water-soluble acrylates copolymer and a water-soluble plasticizer in an aqueous medium provides a product which, upon drying on the skin, including the lips, demonstrates high color intensity, high gloss and excellent long-wearing, transfer-resistant properties.

The compositions of the invention contain substantially no (less than 0.2 weight percent, if present) hydrophobic oils or waxes, and do not require the surfactants and emulsifiers which are employed to stabilize two-phase (emulsion) compositions. Typical hydrophobic oils include those disclosed, for example, in U.S. Pat. Nos. 5,843,407 and 6,780,422, the entire disclosures of which are incorporated by reference, and in the International Cosmetic Ingredient Dictionary and Handbook, twelfth edition, 2004, which also is hereby incorporated by reference. Oils are those materials which are organic substances that are liquid at ambient temperature, such as esters, triglycerides, hydrocarbons and silicones. A typical wax used in cosmetic compositions is carnauba wax. Preferably, the compositions of the present invention do not contain any oils or waxes.

Emulsifiers and surfactants are typically required for use in cosmetic emulsions, which contain normally immiscible water and oil phases, to disperse one of the water and the oil phases in the other phase. Typical emulsifiers and surfactants are disclosed in McCutcheon's, Vol. 1: Emulsifiers and Detergents, North American Edition, 2004, the entire disclosure of which is hereby incorporated by reference. When compositions comprising emulsifiers and/or surfactants are applied to the skin, for example, to the eyelid, the cosmetic film formed when the composition has dried still can bind water (e.g., perspiration) and oil (e.g., skin oils), thereby becoming solubilized, resulting in smudging and reduced length of wear. In contrast to water and oil emulsion compositions, the compositions of the present invention do not contain hydrophobic oils and preferably no oils or; and, therefore, require no emulsifiers and surfactants to stabilize the formulations. The single phase, aqueous compositions of the invention contain truly water-soluble, film-forming copolymers which, when applied to the skin of the eyelid, for example, are not easily solublized, after drying, by either water or oil, and therefore are long-wearing, smudge-resistant and transfer-resistant. If present in the aqueous compositions of the invention, any material which demonstrates emulsifier or surfactant properties will have an HLB of less than 12. Preferably, the compositions of the present invention contain none of the emulsifiers or surfactants which are typically used to stabilize water and oil emulsions.

Preferably, the water-soluble acrylates copolymer will be present in the compositions of the present invention in amounts in the range of from about 1 to about 95 percent, more preferably, in amounts in the range of from about 5 to about 70 percent, and even more preferably, in amounts in the range of from about 10 to about 30 percent, by weight of the total composition.

The water-soluble plasticizer will be present in the composition in an amount sufficient to plasticize, i.e. impart the desired degree of flexibility to, the copolymer. Preferably, the water-soluble plasticizer will be present in the composition in amounts in the range of from about 1 to about 60 percent, and more preferably, in amounts in the range of from about 2 to about 20 percent, by weight of the total composition.

The ratio of the acrylates copolymer to the water-soluble plasticizer in the invention compositions is greater than about 1:1, preferably in the range of from about 2:1 to 20:1, and more preferably in the range of from about 2:1 to 4:1.

Pigment, if present in the invention composition, is preferably present in amounts in the range of about 1 to about 20 percent, and more preferably in amounts in the range of from about 5 to about 15 percent, by weight of the total composition.

The water-soluble acrylates copolymer is an acrylic or methacrylic acid-containing copolymer in which the comonomer may be selected from a wide range of alkyl and alkoxyl acrylates and alkyl and alkoxyl methacrylates. Preferred comonomers include those disclosed in U.S. Pat. No. 5,948,419, the entire disclosure of which is herein incorporated by reference. The comonomers preferably are C1-C8 alkyl acrylates or methacrylates or a C1-C4 alkoxy acrylates or methacrylates, and include, but are not limited to, methyl acrylate, methyl methacrylate, ethyl acrylate, ethyl methacrylate, propyl acrylate, propyl methacrylate, isopropyl acrylate, isopropyl methacrylate, tertiary butyl acrylate, tertiary butyl methacrylate, isobutyl acrylate, isobutyl methacrylate, pentyl acrylate, pentyl methacrylate, isopentyl acrylate, isopentyl methacrylate, neopentyl acrylate, neopentyl methacrylate, hexyl acrylate, hexyl methacrylate, isohexyl acrylate, isohexyl methacrylate, heptyl acrylate, heptyl methacrylate, isoheptyl acrylate, isoheptyl methacrylate, octyl acrylate, octyl methacrylate, isooctyl acrylate, isooctyl methacrylate, 2-ethylhexyl acrylate, 2-ethylhexyl methacrylate, 2-hydroxyethyl (meth)acrylate, polyethylene oxide(meth)acrylates, PEG (meth)acrylates, 3-hydroxypropyl(meth)acrylates, 2-hydroxypropyl(meth)acrylates, polypropylene oxide(meth)acrylates, PPG (meth)acrylates, 3-hydroxybutyl(meth)acrylates, polybutylene oxide(meth)acrylates, or a combination of any two or more of the comonomers. Preferred copolymers may include ethyl acrylate/methyl methacrylate/methacrylic acid; ethyl acrylate/methyl methacrylate/acrylic acid; ethyl acrylate/ethyl methacrylate/methacrylic acid; ethyl acrylate/ethyl methacrylate/acrylic acid; methyl acrylate/methyl methacrylate/methacrylic acid; methyl acrylate/methyl methacrylate/acrylic acid; methyl acrylate/ethyl methacrylate/methacrylic acid; and methyl acrylate/ethyl methacrylate/acrylic acid, particularly ethyl acrylate/methyl methacrylate/methacrylic acid and ethyl acrylate/methyl methacrylate/acrylic acid. Most preferred water-soluble acrylates copolymers for use in the present invention are Covacryl A15® and Covacryl E14® (LCW, France) which are ethyl acrylate/methylmethacrylate/methacrylic acid copolymers. The copolymers differ in their molecular weights and in their monomer to comonomer ratios, and therefore impart different degrees of flexibility/rigidity to the acrylates copolymer in the compositions of the invention.

The water-soluble plasticizer may be selected from polyether derivatives, polyoxypropylene derivatives, glycol and glycol derivatives and glycerin and glycerin derivatives, and combinations thereof. The glycols may include polyethylene glycol, polypropylene glycol and polybutylene glycol. Preferably, the water-soluble plasticizer is an ester, such as, for example, a polyglyceryl ester or a PEG and/or PPG-modified ester, for example, polyglyceryl-3 laurate, PEG-90 diisostearate, PEG/PPG-8/3 laurate, PEG/PPG-8/3 diisostearate, or triisostearoyl polyglyceryl-3 dimer dilinoleate. More preferably, the water-soluble plasticizer is a water-soluble ester, and most preferably, the water-soluble ester is Hydramol PGPD®, Hydramol PGPL®, Hydramol PGDS®, Hydramol TGL® or Schercemol PTID® (Industrial West, N.J.).

Although a wetting property may be attributable to the plasticizer useful in the compositions of the invention, it is not intended that such compounds fall with the scope of the typical emulsifiers and surfactants used in conventional emulsion compositions, such emulsifiers and surfactants being substantially absent from the compositions of the invention. In fact, the plasticizers used in the present compositions could not be used as the sole or principal emulsifying agent to stabilize an emulsion.

The primary function of the water-soluble plasticizer in the compositions of the present invention is as a plasticizer for the copolymer, increasing copolymer flexibility, and resulting in a smooth product when dried down on the skin after application. The water-soluble plasticizer also has a secondary function, acting as a wetting agent for the pigment particles; that is, physically coating the pigment particles and aiding in their dispersion in the system, and imparting brilliant color and shine to the compositions once dried down on the skin.

It is well-recognized that the structural properties of a copolymer are intimately related to the physical arrangement of the monomers residing along the backbone of the chain, and that the structure has a strong influence on the other properties of the copolymer. While not wishing to be bound by any particular theory, it is believed that, in the compositions of the present invention, the water resistance of the product is related to the amount of free or accessible hydroxyl groups remaining in the system after the product is applied to the skin and has dried down. Although the copolymer in the compositions of the present invention is completely water-soluble in the single phase aqueous system, intramolecular hydrogen bonding through hydroxyl and carbonyl groups on individual copolymer chains and intermolecular hydrogen bonding among copolymer chains causes the chains to entangle and to form a network. The water-soluble plasticizer also has a high hydroxyl group content such that intermolecular hydrogen bonding also occurs between the plasticizer and the copolymer chains in the network. Once the network is formed in the system (i.e., gellation occurs), the composition is not easily solubilized, since penetration of the network by water or oil molecules is greatly limited. Additionally, as a result of the formation of the network, the number of free or accessible hydroxyl groups is greatly reduced, and those free hydroxyl groups are internalized in the network. Surprisingly, therefore, although the copolymer and the plasticizer are water-soluble in the single phase aqueous composition, once the composition is applied to skin, and dries down (i.e., the water evaporates), the composition is water-resistant, in view of the reduced number of accessible hydroxyl groups available for solubilization if contacted with water. Since the single phase aqueous system contains substantially no oil and, as such, does not require the presence of emulsifiers or surfactants, and since the plasticizer (e.g., water-soluble ester) also is tied up in the network, any potentially oil compatible portions, too, are inaccessible to oil. For this further reason the plasticizer would be inaccessible to function as an emulsifier or surfactant.

The compositions of the present invention optionally include a pigment selected from cosmetically acceptable inorganic and organic pigments, such as those disclosed in the International Cosmetic Ingredient Dictionary and Handbook, twelfth edition, 2004, the entire disclosure of which is herein incorporated by reference. Pigments suitable for use in the invention compositions include those disclosed in U.S. Pat. No. 6,726,900, the entire disclosure of which is incorporated herein by reference. The inorganic pigments may include red, black, green and yellow iron oxides, titanium dioxide, bismuth oxychloride and the like. Particularly preferred organic pigments are D&C and FD&C colors, including red, green, blue, yellow, violet, orange, Lakes thereof and mixtures thereof, including FD&C colors Blue 1, Blue 2, Green 3, Orange B, Citrus Red 2, Red 3, Red 4, Red 40, Yellow 5, Yellow 6, Blue 1, Blue 2; Orange B, Citrus Red 2; and the D&C colors Blue 4, Blue 9, Green 5, Green 6, Green 8, Orange 4, Orange 5, Orange 10, Orange 11, Red 6, Red 7, Red 17, Red 21, Red 22, Red 27, Red 28, Red 30, Red 31, Red 33, Red 34, Red 36, Red 39, Violet 2, Yellow 7, Yellow 8, Yellow 10, Yellow 11, Blue 4, Blue 6, Green 5, Green 6, Green 8, Orange 4, Orange 5, Orange 10, Orange 11, and so on. Particularly preferred lakes are formed by the reaction of the organic pigment with a metallic salt such as aluminum, calcium, zirconium, barium, and the like. Suitable reds include pigments from the monoazo, disazo, fluoran, xanthene, or indigoid families or lakes thereof, such as Red 4, 6, 7, 17, 21, 22, 27, 28, 30, 31, 33, 34, 36, and Red 40. Also suitable are lakes of such red pigments. Typically, the metal salts are aluminum, barium, and the like. The yellow pigment may be a pyrazole, monoazo, fluoran, xanthene, quinoline, or salt thereof. Suitable yellows include Yellow 5, 6, 7, 8, 10, and 11, as well as lakes of such yellow pigments. Suitable violets include those from the anthroquinone family, such as Violet 2 and lakes thereof. Examples of orange pigments are Orange 4, 5, 10, 11, or lakes thereof.

A preferred composition according to the present invention consists essentially of from about 10 to about 30 weight percent ethyl acrylate/methylmethacrylate/methacrylic acid copolymer, and from about 2 to about 20 weight percent PEG-90 diisostearate and PEG/PPG-8/3-laurate, by total weight of the composition.

A further preferred composition according to the present invention consists essentially of from about 10 to about 30 weight percent ethyl acrylate/methylmethacrylate/methacrylic acid copolymer, and from about 2 to about 20 weight percent PEG-90 diisostearate, by total weight of the composition.

Yet a further preferred composition according to the present invention consists essentially of from about 10 to about 30 weight percent ethyl acrylate/methylmethacrylate/methacrylic acid copolymer; from about 2 to about 20 weight percent PEG-90 diisostearate and PEG/PPG-8/3-laurate; and from about 5 to about 15 weight percent black iron oxide, by total weight of the composition.

Still a further preferred composition according to the present invention consists essentially of from about 10 to about 30 weight percent ethyl acrylate/methylmethacrylate/methacrylic acid copolymer; from about 2 to about 20 weight percent PEG-90 diisostearate; and from about 5 to about 15 weight percent black iron oxide, by total weight of the composition.

The compositions may include further components, such as one or more water-dispersible plasticizers, for example, water-dispersible esters, such as Covaplast® (LCW, France), antimicrobials, preservatives, stabilizers, suspending agents or thickeners, water-soluble actives and combinations thereof.

Typical preservatives which may be used in the invention compositions include, for example, ethylhexylglycerin and caprylyl glycol/phenoxyethanol/hexylene glycol. Other preservatives suitable for use in the compositions are disclosed in the International Cosmetic Ingredient Dictionary and Handbook, twelfth edition, 2004.

Suitable structuring agents, i.e., stabilizers, suspending agents and/or thickeners, for use in the invention compositions include, but are not limited to PVP copolymers, such as ammonium acrylodimethyltaurate/VP polymer; cellulose derivatives, for example, hydroxyethylcellulose and sodium carboxymethylcellulose; acrylates, such as glyceryl polyacrylate; polysaccharide derivatives, for example, sclerotium gel; modified corn starch; silicates, such as magnesium aluminum silicate and sodium magnesium silicate; hectorite and derivatives, such as Bentones; xanthan gum; and kaolin. Additional structuring agents are disclosed in McCutcheon's Volume 2: Functional Materials, North American Edition, 2004, the entire disclosure of which is hereby incorporated by reference.

Water-soluble actives which may be used in the compositions of the invention include, but are not limited to, sunscreens (such as Eusolex 232); and antioxidants, for example ginkgo-biloba, beta carotene, green tea, ascorbic acid and derivatives thereof such as sodium ascorbyl phosphate and magnesium ascorbyl phosphate and carnosic acid (rosemary).

The compositions of the invention may be embodied in, for example, eyeliner, mascara, concealer, lip gloss and lipliner.

The following non-limiting examples further illustrate the embodiments of the invention.

EXAMPLES

Example 1

Eyeliner Formulation

TABLE 1

| MATERIAL | WEIGHT PERCENT |
| --- | --- |
| sequence 1 | |
| purified water | 20.00 |
| magnesium aluminum silicate | 0.50 |
| cellulose gum | 0.20 |
| xanthan gum | 0.20 |
| ethylhexylglycerin | 0.25 |
| sequence 2 | |
| purified water | 6.75 |
| ethylhexylglycerin | 0.25 |
| iron oxides | 13.00 |
| sequence 3 | |
| acrylates copolymer (Covacryl A15) | 9.80 |
| acrylates copolymer (Covacryl E14) | 4.00 |
| caprylylglycol/phenoxyethanol/hexylene glycol | 0.13 |
| ethylhexylglycerin | 0.25 |
| sequence 4 | |
| PEG-90 diisostearate (Hydramol PGDS) | 2.70 |
| PEG/PPG-8/3 laurate (Hydramol PGPL) | 1.28 |
| caprylylglycol/phenoxyethanol/hexylene glycol | 0.15 |
| ethylhexylglycerin | 0.25 |
| sequence 5 | |
| kaolin | 5.00 |
| sequence 6 | |
| purified water | 35.30 |
| TOTAL | 100.00 |

With reference to Table 1, pure water and ethylhexylglycerin were heated to 50° C. Magnesium aluminum silicate, cellulose gum and xanthan gum were sprinkled into the water and ethylhexylglycerin mixture separately and stirred until the mixture gelled. The temperature of the mixture was reduced to 25° C. forming sequence 1. Sequence 2 materials were milled together and added to the sequence 1 mixture. The materials of sequence 3 were added to the above mixture. The materials of sequences 4, 5 and 6 were then sequentially added to the above mixture. The product prepared was intensely black and shiny and transfer-resistant.

In examples 2 through 5 (Tables 2 through 5), the materials of sequence 1 were combined and mixed until uniform, the materials of sequence 2 were milled together and added to the sequence 1 mixture. The materials of each additional sequence were added to the above mixture and mixed together until uniform. The eyeliner formulations of the invention are given below in Tables 2 through 5.

Example 2

Eyeliner Formulation

TABLE 2

| MATERIAL | WEIGHT PERCENT |
|---|---|
| sequence 1 | |
| acrylates copolymer (Covacryl A15) | 9.80 |
| acrylates copolymer (Covacryl E14) | 4.00 |
| caprylyl glycol/phenoxyethanol/hexylene glycol | 0.25 |
| ethylhexylglycerin | 0.50 |
| sequence 2 | |
| purified water | 6.75 |
| ethylhexylglycerin | 0.25 |
| iron oxides (cosmetic black) | 13.00 |
| sequence 3 | |
| PEG-90 diisostearate (Hydramol PGDS) | 6.00 |
| PEG/PPG-8/3 laurate (Hydramol PGPL) | 6.00 |
| caprylylglycol/phenoxyehtanol/hexylene glycol | 0.25 |
| ethylhexylglycerin | 0.25 |
| sequence 4 | |
| purified water | 52.95 |
| TOTAL | 100.00 |

Example 3

Eyeliner Formulation

TABLE 3

| MATERIAL | WEIGHT PERCENT |
|---|---|
| sequence 1 | |
| acrylates copolymer (Covacryl E14) | 15.00 |
| sequence 2 | |
| purified water | 36.50 |
| iron oxides (cosmetic black) | 10.00 |
| sequence 3 | |
| kaolin | 30.00 |

TABLE 3-continued

| MATERIAL | WEIGHT PERCENT |
|---|---|
| sequence 4 | |
| PEG-90 diisostearate (Hydramol PGDS) | 0.50 |
| PEG/PPG-8/3 laurate (Hydramol PGPL) | 8.00 |
| TOTAL | 100.00 |

Example 4

Eyeliner Formulation

TABLE 4

| MATERIAL | WEIGHT PERCENT |
|---|---|
| sequence 1 | |
| acrylates copolymer (Covacryl A15) | 15.00 |
| acetyl tributyl citrate, tr trioctyltrimellitate, triethyl citrate | 0.50 |
| sequence 2 | |
| iron oxides | 12.50 |
| purified water | 7.50 |
| sequence 3 | |
| PEG-90 diisostearate (Hydramol PGDS) | 2.70 |
| PEG/PPG-8/3 laurate (Hydramol PGPL) | 1.28 |
| sequence 4 | |
| kaolin | 6.00 |
| sequence 5 | |
| purified water | 54.52 |
| TOTAL | 100.00 |

Example 5

Eyeliner Formulation

TABLE 5

| MATERIAL | WEIGHT PERCENT |
|---|---|
| sequence 1 | |
| acrylates copolymer (Covacryl A15) | 9.80 |
| acrylates copolymer (Covacryl E14) | 4.00 |
| sequence 2 | |
| iron oxides | 12.50 |
| purified water | 7.50 |
| sequence 3 | |
| PEG-90 diisostearate (Hydramol PGDS) | 3.00 |
| sequence 4 | |
| kaolin | 6.00 |
| sequence 5 | |
| purified water | 57.20 |
| TOTAL | 100.00 |

Example 6

Lip Gloss Formulation

TABLE 6

| MATERIALS | WEIGHT PERCENT |
|---|---|
| sequence 1 | |
| acrylates copolymer (Covacryl A15) | 7.68 |
| acrylates copolymer (Covacryl E14) | 3.42 |
| purified water | 35.90 |
| sequence 2 | |
| purified water | 10.00 |
| titanium dioxide | 1.42 |
| iron oxides (pure oxy red 78054/3080) | 0.63 |
| D&C red no. 7 calcium lake (C19-011) | 0.60 |
| iron oxides (cosmetic yellow C-33-8073/CG490) | 0.34 |
| iron oxides (pure oxy black 7053/3068) | 0.25 |
| sequence 3 | |
| mica/titanium dioxide (Timiron MP-1005 supersilk) | 1.00 |
| sequence 4 | |
| PEG-90 diisostearate (Hydramol PGDS) | 3.00 |
| PEG/PPG-8/3 laurate (Hydramol PGPL) | 3.00 |
| sequence 5 | |
| purified water | 30.00 |
| hectorite (Bentone EW) | 0.60 |
| caprylyl glycol/phenoxyethanol/hexylene glycol | 0.50 |
| ethylhexylglycerin | 0.50 |
| sequence 6 | |
| purified water | 1.16 |
| TOTAL | 100.00 |

With reference to Table 6, sequence 1 materials were mixed until uniform. Sequence 2 materials were milled together until uniform and added to the sequence 1 mixture. Sequence 3 and 4 materials were sequentially added to the above mixture, and mixed until uniform. Sequence 5 materials were premixed, heated to 75° C. until uniform, and added to the above mixture. The mixture was then mixed at room temperature until uniform. The product prepared was glossy, vivid in color, transfer-resistant, and comfortable on the lips.

Example 7

Lip Gloss Formulation

TABLE 7

| MATERIALS | WEIGHT PERCENT |
|---|---|
| sequence 1 | |
| acrylates copolymer (Covacryl A15) | 7.68 |
| acrylates copolymer (Covacryl E14) | 3.42 |
| purified water | 35.90 |
| sequence 2 | |
| PEG-90 diisostearate (Hydramol PGDS) | 3.00 |
| PEG/PPG-8/3 laurate (Hydramol PGPL) | 3.00 |
| sequence 3 | |
| purified water | 30.00 |
| caprylyl glycol/phenoxyethanol/hexylene glycol | 0.50 |
| ethylhexylglycerin | 0.50 |
| sequence 4 | |
| purified water | 16.00 |
| TOTAL | 100.00 |

The composition of Example 7 was prepared in the same manner as the composition of Example 6 except that the latter was a nonpigmented lipgloss.

Example 8

Comparative Gloss Test

TABLE 8

| MATERIALS | WEIGHT PERCENT |
|---|---|
| sequence 1 | |
| acrylates copolymer (Covacryl A15) | 9.80 |
| acrylates copolymer (Covacryl E14) | 4.00 |
| caprylyl glycol/phenoxyethanol/hexylene glycol | 0.15 |
| purified water | 32.10 |
| sequence 2 | |
| purified water | 23.94 |
| caprylyl glycol/phenoxyethanol/hexylene glycol | 0.15 |
| Ethylhexylglycerin | 0.13 |
| iron oxides (cosmetic black) | 12.75 |
| sequence 3 | |
| kaolin | 6.30 |
| caprylyl glycol/phenoxyethanol/hexylene glycol | 0.20 |
| sequence 4 | |
| PEG-90 diisostearate (Hydramol PGDS) | 2.70 |
| PEG/PPG-8/3 laurate (Hydramol PGPL) | 1.28 |
| purified water | 6.30 |
| caprylyl glycol/phenoxyethanol/hexylene glycol | 0.20 |
| TOTAL | 100.00 |

An eyeliner formulation having the components shown in Table 8 was prepared by mixing sequence 1 materials together at room temperature until uniform, milling together sequence 2 materials, adding the milled sequence 2 materials to the sequence 1 mixture and mixing until uniform. Sequence 3 materials were added to the mixture of sequence 1 and 2 materials, followed by the addition of the sequence 4 materials, mixing until uniform. Test samples (5 mm wet thickness) of the formulation of the invention (sample A) and three comparative eyeliner product emulsion formulations (samples B, C and D) were cast on Leneth card (form 2A-Opacity) within a 1"×2" area. The samples were sufficiently thick (opaque) to avoid background reflectance. The samples were permitted to dry. Light was flashed at the samples at angles of 20° and 60°. The reflectance (scale of 0-100 gloss units) for each sample was measured at angles of 20° and 60°, using a gloss meter from BYK Garden; Model: micro-TRI-gloss dried. As indicated in Table 9 below, the inventive composition (A) demonstrated a higher gloss than any of the comparative emulsion compositions (B-D).

TABLE 9

| SAMPLE | GLOSS UNITS | |
| --- | --- | --- |
| | 20° | 60° |
| A (inv) | 0.5 | 5.4 |
| B (comp) | 0.2 | 2.1 |
| C (comp) | 0.1 | 0.4 |
| D (comp) | 0.1 | 1.7 |

Note:
Comparative sample B contains greater than 0.2 weight percent oil (Carnauba wax).
Comparative sample C contains greater than 0.2 weight percent oil (neopentyl glycol/C13-C14 isoparaffin).
Comparative sample C contains greater than 0.2 weight percent oil (oleyl alcohol).

Example 9

Evaluation of Water-based Eyeliner for Transfer-resistance

A study was done to determine the resistance of the eyeliner formulation shown in Table 8 to wear and flaking. Eight adult women participated in the study. The volunteer panelists were in normal health with no evidence of a systemic illness, nor any dermatogical disorder in the areas used in the study, which conditions might interfere with the analysis of the test results. Pregnant or lactating volunteers were excluded from the study. Panelists used for the study were not using systemic or topical retinoids, antihistamines or similar agents during the course of the study and two weeks prior to commencement of the study.

The women were instructed to wear no moisturizer or makeup for the test. The test sites were the eyelids. The panelists were given a sample of liquid eyeliner and instructed to apply the eyeliner as evenly as possible to the top and the bottom eyelids.

Wear and flaking evaluations were carried out immediately after product application, and two, four, six and eight hours after application.

Wear and flaking were assessed via photography using a Fuji S2 digital camera. The panelist's head was fixed in a headrest (Canfield Scientific) to which the camera was mounted. The camera lens was set at a distance of 0.35 m from the area to be photographed. Close up photographs of the eye area were taken at two, four, six and eight hours after application. The photographs were stored and viewed on Canfield Photofile Image Management Software (version 4.5.148). Clinical evaluations of the photographs were conducted by a trained investigator using a 10-point analog scale (shown below). The investigator was trained and qualified by an outside consultant to objectively identify and quantify the characteristics of skin parameters. The investigator had an extensive perceptual vocabulary, and was experienced in scale usage and the use of standardized evaluation techniques. A standard lexicon and references specifically for each of wear and flaking parameters (i.e. a photo scale depicting what a "0" looks lie, what a "2" looks like, etc. up to "10") were used for evaluation. "Wear" was defined as the visual observation of the amount of product color appearing and the amount of natural skin color that is visible at the indicated time points after application. "Flaking" was defined as the visual observation of the number of pieces of product falling onto the skin around the eyes or into the eyes at the indicated time points after application.

| 10 point scale | |
| --- | --- |
| 0 | 10 |
| No wear | Extreme wear |
| No flaking | Extreme flaking |

The results of the clinical evaluation are shown in Table 10 below. After 8 hours of wear, the eyeliner composition of the invention demonstrated minimal wear and minimal flaking.

TABLE 10

| Time After Application | Observed Wear | Observed Flaking |
| --- | --- | --- |
| 0 | 0.0 (none) | 0.0 (none) |
| 2 | 0.0 (none) | 0.0 (none) |
| 4 | 0.0 (none) | 0.0 (none) |
| 6 | 0.4 (minimal) | 0.0 (none) |
| 8 | 0.8 (minimal) | 0.7 (minimal) |

While the invention has been described in connection with preferred embodiments, it not intended to limit the scope of the invention to the particular forms set forth, but it is intended to cover such alternative modifications and equivalents as may be included within the spirit and scope of the invention as defined by the appended claims.

We claim:
1. A transfer-resistant, single phase aqueous cosmetic composition, consisting essentially of
   (a) a water-soluble film-forming acrylates copolymer consisting essentially of a monomer selected from the group consisting of acrylic acid and methacrylic acid and a comonomer selected from the group consisting of alkyl and alkoxyl acrylates and alkyl and alkoxyl methacrylates;
   (b) a water-soluble plasticizer for the copolymer which is an ester selected from the group consisting of polyglyceryl-3 laurate, PEG-90 diisostearate, PEG/PPG-8/3 laurate, PEG/PPG-8/3 diisostearate, triisostearoyl polyglyceryl-3 dimer dilinoleate, and mixtures thereof, wherein the water-soluble plasticizer cannot function as a sole or principal emulsifier to stabilize an emulsion, and wherein the water-soluble acrylates copolymer and the water-soluble plasticizer are present in the composition in a ratio in the range of from about 2:1 to 20:1;
   (c) pigment; and
   (d) water;
   wherein the water-solubility of the copolymer and the plasticizer for the copolymer enable intramolecular hydrogen bonding through hydroxyl and carbonyl groups on individual copolymer chains, intermolecular hydrogen bonding among the copolymer chains, and hydrogen bonding between the copolymer chains and hydroxyl groups of the plasticizer causing the copolymer chains to entangle one another and entrap the plasticizer into a network, the composition containing substantially no oil or wax or oil-soluble film-former which could prevent formation of or disrupt integrity of the network, and wherein once the network is formed and the water evaporates, a film thus-produced is water- and oil-resistant.

2. The cosmetic composition according to claim 1, wherein the comonomer comprises a C1-C8 alkyl acrylate or methacrylate or a C1-C4 alkoxy acrylate or methacrylate.

3. The cosmetic composition according to claim 2, wherein the comonomer is selected from the group consisting of methyl acrylate, methyl methacrylate, ethyl acrylate, ethyl methacrylate, propyl acrylate, propyl methacrylate, isopropyl acrylate, isopropyl methacrylate, tertiary butyl acrylate, tertiary butyl methacrylate, isobutyl acrylate, isobutyl methacrylate, pentyl acrylate, pentyl methacrylate, isopentyl acrylate, isopentyl methacrylate, neopentyl acrylate, neopentyl methacrylate, hexyl acrylate, hexyl methacrylate, isohexyl acrylate, isohexyl methacrylate, heptyl acrylate, heptyl methacrylate, isoheptyl acrylate, isoheptyl methacrylate, octyl acrylate, octyl methacrylate, isooctyl acrylate, isooctyl methacrylate, 2-ethylhexyl acrylate, 2-ethylhexyl methacrylate, and mixtures thereof.

4. The composition according to claim 1, wherein the copolymer is selected from the group consisting of ethyl acrylate/methyl methacrylate/methacrylic acid; ethyl acrylate/methyl methacrylate/acrylic acid; ethyl acrylate/ethyl methacrylate/methacrylic acid; ethyl acrylate/ethyl methacrylate/acrylic acid; methyl acrylate/methyl methacrylate/methacrylic acid; methyl acrylate/methyl methacrylate/acrylic acid; methyl acrylate/ethyl methacrylate/methacrylic acid; methyl acrylate/ethyl methacrylate/acrylic acid, and mixtures thereof.

5. The composition according to claim 4, wherein the copolymer is ethyl acrylate/methyl methacrylate/methacrylic acid, ethyl acrylate/methyl methacrylate/acrylic acid or a mixture thereof.

6. The cosmetic composition according to claim 1, wherein the water-soluble acrylates copolymer is present in an amount in the range of from about 1 to about 95 percent by weight of the total composition.

7. The cosmetic composition according to claim 6, wherein the water-soluble acrylates copolymer is present in an amount in the range of from about 5 to about 70 percent by weight of the total composition.

8. The cosmetic composition according to claim 7, wherein the water-soluble acrylates copolymer is present in an amount in the range of from about 10 to about 30 percent by weight of the total composition.

9. The cosmetic composition according to claim 1, wherein the water-soluble plasticizer is present in an amount in the range of from about 1 to about 60 percent by weight of the total composition.

10. The cosmetic composition according to claim 9, wherein the water-soluble plasticizer is present in an amount in the range of from about 2 to about 20 percent by weight of the total composition.

11. The cosmetic composition according to claim 1, wherein the ratio of the water-soluble acrylates copolymer to the water-soluble ester is in the range of from about 2:1 to 4:1.

12. The cosmetic composition according to claim 1, wherein the pigment is a cosmetically acceptable inorganic pigment selected from the group consisting of red, blue, black, green and yellow iron oxides, titanium dioxide, bismuth oxychloride, and mixtures thereof.

13. The cosmetic composition according to claim 1, wherein the pigment is a cosmetically acceptable organic pigment selected from the group consisting of red, orange, yellow, green, blue and violet D&C colors, FD&C colors, or Lakes of D&C or FD&C colors and mixtures thereof.

14. The cosmetic composition according to claim 1, wherein the pigment is present in a range of from about 1 to about 20 percent by weight of the total composition.

15. The cosmetic composition according to claim 1, which is an eyeliner, a mascara, a concealer, a lipgloss or a lipliner.

16. The transfer-resistant, single phase aqueous cosmetic composition according to claim 1 consisting essentially of water, from about 10 to about 30 weight percent ethyl acrylate/methylmethacrylate/methacrylic acid copolymer; from about 2 to about 20 weight percent PEG-90 diisostearate and PEG/PPG-8/3-laurate; and from about 5 to about 15 weight percent black iron oxide, based on the total weight of the composition.

17. The transfer-resistant, single phase aqueous cosmetic composition according to claim 1 consisting essentially of water, from about 10 to about 30 weight percent ethyl acrylate/methylmethacrylate/methacrylic acid copolymer; from about 2 to about 20 weight percent PEG-90 diisostearate; and from about 5 to about 15 weight percent black iron oxide, by total weight of the composition.

18. A transfer-resistant, single phase aqueous cosmetic composition consisting essentially of
  (a) a water-soluble film-forming acrylates copolymer consisting essentially of a monomer selected from the group consisting of acrylic acid and methacrylic acid and a comonomer selected from the group consisting of alkyl and alkoxyl acrylates and alkyl and alkoxyl methacrylates; and
  (b) a water-soluble plasticizer for the copolymer which is an ester selected from the group consisting of polyglyceryl-3 laurate, PEG-90 diisostearate, PEG/PPG-8/3 laurate, PEG/PPG-8/3 diisostearate, triisostearoyl polyglyceryl-3 dimer dilinoleate, and mixtures thereof, wherein the water-soluble plasticizer cannot function as a sole or principal emulsifier to stabilize an emulsion, and wherein the water-soluble acrylates copolymer and the water-soluble plasticizer are present in the composition in a ratio in the range of from about 2:1 to 20:1; and
  (c) water;
  wherein the water-solubility of the copolymer and the plasticizer for the copolymer enable intramolecular hydrogen bonding through hydroxyl and carbonyl groups on individual copolymer chains, intermolecular hydrogen bonding among the copolymer chains, and hydrogen bonding between the copolymer chains and hydroxyl groups of the plasticizer causing the copolymer chains to entangle one another and entrap the plasticizer into a network, the composition containing substantially no oil or wax or oil-soluble film-former which could prevent formation of or disrupt integrity of the network, and wherein once the water evaporates, a film thus-formed is water- and oil-resistant.

19. The cosmetic composition according to claim 18, wherein the comonomer comprises a C1-C8 alkyl acrylate or methacrylate or a C1-C4 alkoxyl acrylate or methacrylate.

20. The composition according to claim 18, wherein the copolymer is selected from the group consisting of ethyl acrylate/methyl methacrylate/methacrylic acid; ethyl acrylate/methyl methacrylate/acrylic acid; ethyl acrylate/ethyl methacrylate/methacrylic acid; ethyl acrylate/ethyl methacrylate/acrylic acid; methyl acrylate/methyl methacrylate/methacrylic acid; methyl acrylate/methyl methacrylate/acrylic acid; methyl acrylate/ethyl methacrylate/methacrylic acid; methyl acrylate/ethyl methacrylate/acrylic acid, and mixtures thereof.

21. The composition according to claim 20, wherein the copolymer is ethyl acrylate/methyl methacrylate/methacrylic acid, ethyl acrylate/methyl methacrylate/acrylic acid or a mixture thereof.

22. The cosmetic composition according to claim 18, wherein the copolymer is present in an amount in the range of from about 10 to about 30 percent by weight of the total composition.

23. The cosmetic composition according to claim 18, wherein the plasticizer is present in an amount in the range of from about 2 to about 20 percent by weight of the total composition.

24. The cosmetic composition according to claim 23, wherein the ratio of the acrylates copolymer to the plasticizer is in the range of from about 2:1 to 4:1.

25. The cosmetic composition according to claim 18, in which oil or wax, if present, is present in an amount of no greater than 0.2 weight percent, by weight of the total composition.

26. The transfer-resistant, single phase aqueous cosmetic composition according to claim 18 consisting essentially of water, from about 10 to about 30 weight percent ethyl acrylate/methylmethacrylate/methacrylic acid copolymer, and from about 2 to about 20 weight percent PEG-90 diisostearate and PEG/PPG-8/3-laurate, by weight of the total composition.

27. The transfer-resistant, single phase aqueous cosmetic composition according to claim 18 consisting essentially of water, from about 10 to about 30 weight percent ethyl acrylate/methylmethacrylate/methacrylic acid copolymer, and from about 2 to about 20 weight percent PEG-90 diisostearate, by weight of the total composition.

28. A method of improving the transfer-resistance and/or the shine of a cosmetic composition, comprising combining ingredients consisting essentially of:
 (a) a water-soluble film-forming acrylates copolymer copolymers consisting essentially of a monomer selected from the group consisting of acrylic acid and methacrylic acid and a comonomer selected from the group consisting of alkyl and alkoxyl acrylates and alkyl and alkoxyl methacrylates;
 (b) a water-soluble plasticizer for the copolymer; which is an ester selected from the group consisting of polyglyceryl-3 laurate, PEG-90 diisostearate, PEG/PPG-8/3 laurate, PEG/PPG-8/3 diisostearate, triisostearoyl polyglyceryl-3 dimer dilinoleate, and mixtures thereof, wherein the water-soluble plasticizer cannot function as a sole or principal emulsifier to stabilize an emulsion, and wherein the water-soluble acrylates copolymer and the water-soluble plasticizer are present in the composition in a ratio in the range of from about 2:1 to 20:1; and
 (c) water;
 wherein the water-solubility of the copolymer and the plasticizer for the copolymer enable intramolecular hydrogen bonding through hydroxyl and carbonyl groups on individual copolymer chains, intermolecular hydrogen bonding among the copolymer chains, and hydrogen bonding between the copolymer chains and hydroxyl groups of the plasticizer causing the copolymer chains to entangle one another and entrap the plasticizer into a network, the composition containing substantially no oil or wax or oil-soluble film-former which could prevent formation of or disrupt integrity of the network, and wherein once the water evaporates, the film thus-formed is water- and oil-resistant.

29. The method according to claim 28, wherein the composition further comprises a pigment.

30. A method of redefining the lipline, comprising:
 (a) providing a first transfer-resistant single phase aqueous composition comprising a water-soluble film-forming acrylates copolymer consisting essentially of
  (1) a water-soluble film-forming acrylates copolymer consisting essentially of a monomer selected from the group consisting of acrylic acid and methacrylic acid and a comonomer selected from the group consisting of alkyl and alkoxyl acrylates and alkyl and alkoxyl methacrylates;
  (2) a water-soluble plasticizer for the copolymer which is an ester selected from the group consisting of polyglyceryl-3 laurate, PEG-90 diisostearate, PEG/PPG-8/3 laurate, PEG/PPG-8/3 diisostearate, triisostearoyl polyglyceryl-3 dimer dilinoleate, and mixtures thereof, wherein the water-soluble plasticizer cannot function as a sole or principal emulsifier to stabilize an emulsion, and wherein the water-soluble acrylates copolymer and the water-soluble plasticizer are present in the composition in a ratio in the range of from about 2:1 to 20:1;
  (3) pigment having a natural lip color; and
  (4) water;
 wherein water-solubility of the copolymer and the plasticizer for the copolymer enable intramolecular hydrogen bonding through hydroxyl and carbonyl groups on individual copolymer chains, intermolecular hydrogen bonding among the copolymer chains, and hydrogen bonding between the copolymer chains and hydroxyl groups of the plasticizer causing the copolymer chains to entangle one another and entrap the plasticizer into a network, the composition containing substantially no oil or wax or oil-soluble film-former which could prevent formation of or disrupt integrity of the network, and wherein once the water evaporates, a film thus-formed is water- and oil-resistant;
 (b) providing a second transfer-resistant single phase aqueous composition consisting essentially of
  (1) a water-soluble film-forming acrylates copolymer consisting essentially of a monomer selected from the group consisting of acrylic acid and methacrylic acid and a comonomer selected from the group consisting of alkyl and alkoxyl acrylates and alkyl and alkoxyl methacrylates;
  (2) a water-soluble plasticizer for the copolymer which is an ester selected from the group consisting of polyglyceryl-3 laurate, PEG-90 diisostearate, PEG/PPG-8/3 laurate, PEG/PPG-8/3 diisostearate, triisostearoyl polyglyceryl-3 dimer dilinoleate, and mixtures thereof, wherein the water-soluble plasticizer cannot function as a sole or principal emulsifier to stabilize an emulsion, and wherein the water-soluble acrylates copolymer and the water-soluble plasticizer are present in the composition in a ratio in the range of from about 2:1 to 20:1;
  (3) pigment having a desired color; and
  (4) water;
 wherein water-solubility of the copolymer and the plasticizer for the copolymer enable intramolecular hydrogen bonding through hydroxyl and carbonyl groups on individual copolymer chains, intermolecular hydrogen bonding among the copolymer chains, and hydrogen bonding between the copolymer chains and hydroxyl groups of the plasticizer causing the copolymer chains to entangle one another and entrap the plasticizer into a network, the composition containing substantially no oil or wax or oil-soluble film-former which could prevent formation of or disrupt integrity of the network, and wherein once the water evaporates, a film thus-formed is water- and oil-resistant;
 (c) dipping a lipliner brush into the composition having the natural lip color so as to load the brush with the composition;

(d) tracing a line with the lipliner brush just inside or just outside a user's natural lipline;
(e) allowing the traced line to dry;
(f) dipping a lipliner brush into the composition having the desired lip color so as to load the brush with the composition; and
(g) applying the desired color composition within the redefined lipline.

\* \* \* \* \*